US00PP09252P

United States Patent [19]

Williams

[11] Patent Number: Plant 9,252

[45] Date of Patent: Aug. 22, 1995

[54] MINIATURE ROSE PLANT NAMED 'MICPAL'

[76] Inventor: Michael C. Williams, P.O. Box 203, Cross Hill, S.C. 29332

[21] Appl. No.: 178,871

[22] Filed: Jan. 7, 1994

[51] Int. Cl.[6] ..... A01H 5/00
[52] U.S. Cl. ..... Plt./7.1
[58] Field of Search ..... Plt. 7.1, 10.1

[56] References Cited

U.S. PATENT DOCUMENTS

P.P. 4,292 8/1978 Schwartz ..... Plt./7.1

*Primary Examiner*—Howard J. Locker

[57] ABSTRACT

This new and distinct variety of miniature rose plant is characterized by blended yellow and orange buds and blooms, with hues depending upon light intensity and heat intensity. The plant is characterized further by its vigorous, upright growth, and semi-glossy green foliage.

1 Drawing Sheet

BACKGROUND OF NEW VARIETY

The present introduction of a new and distinct variety of rose plant of the miniature rose class, which was created by my crossing as seed parent the miniature rose "Orange Honey" (U.S. Plant Pat. No. 4,496) and as pollen parent an unnamed miniature rose seedling, has the varietal denomination of "Micpal".

Among the distinguishing characteristics possessed by this new variety which separate it from its parents and all other varieties of which I am aware are abundant yellow and orange blended blooms on a vigorous plant with abundant foliage.

The present variety of miniature rose was originated by me in Laurens County, S.C. Asexual reproduction by cuttings of the new variety as performed by me in Laurens County, S.C., has shown conclusively that the foregoing and other distinguishing characteristics come true to form and are established and faithfully transmitted through succeeding propogations.

BRIEF DESCRIPTION OF PHOTOGRAPH

The accompanying photograph shows typical specimens of the vegetative growth and flowers of the new variety in different stages of development and as depicted in color as nearly true as it is reasonably possible to make the same in a color photograph of this character.

DETAILED BOTANICAL DESCRIPTION OF NEW VARIETY

The following is a detailed description of my new rose variety, with color terminology is accordance with the plate numbers of The Royal Horticultural Society Colour Chart except where common dictionary terms of color definitions are employed.

Breeding: Seedling.

*Seed parent.*—Orange Honey (U.S. Plant Pat. No. 4,496).

*Pollen parent.*—Unnamed miniature seedling.

Class: Miniature rose.

Variety: Micpal.

Blooming habit: Continuous.

The following observations were made from specimens grown outdoors in Laurens Country, S.C., U.S.A., in September 1993.

FLOWER

A. Bud:

(1) *Size.*—Circumference — 2 to 2.5 inches. Diameter — $\frac{3}{8}$ to $\frac{1}{2}$ inch.

(2) *Form.*—High centered urn shape.

(3) *Color.*—When sepals first divide — 20C with 28A visible along the very edge of the first petals. When petals begin to unfurl — 21D flushed with 28C. Half-blown: inside of petals — 21D at the base of petal blends with 33B toward the center of the petal and shades to 34B on the outer edge of the petals. reverse side of petals — 14B with a bush of 34B on the petal edge.

(4) *Sepals.*—Extending from $\frac{1}{8}$ to $\frac{1}{4}$ inch beyond tip of bud before opening. Very slightly foliated. Sepal color is 137D outerside and 138C inside.

(5) *Peduncle.*—Length: 1 to 1.5 inches. Aspect: Generally smooth and straight. Strength: Erect. Color: New Growth — 185B. Old growth — 137B.

B. Bloom:

(1) *Size.*—Average size when fully expanded: 2 inches.

(2) *Bonne.*—Singly, occasionally with two side buds.

(3) *Form.*—High centered blooms. Outer 2 or 3 rows of petals are quilled. Inner petals more reflexed.

(4) *Petalage.*—Number of petals under normal conditions: 20–25.

(5) *Color*(during first days).—Inner surface of petals at center of flower — 10B flushed with 32C. Inner surface of outer petals — 10C flushed with 29A. Base of petals (point of attachment) — 15D. Underside/petal reverse — 14C slightly blushed with 33C. General tonality from a distance — 10C blended with 32D.

(6) *Color change.*—As bloom ages — All colors become lighter shades with the base of the petals being 5D and the remaining part of the petal fading to 29C/D.

C. Petals:

(1) *Texture.*—Soft, medium thickness.
(2) *Appearance.*—Inside — velvety, outside — satiny.
(3) *Form.*—Oval shaped.
(4) *Arrangement.*—Regular.
(5) *Petaloids in center.*—Six or less.
(6) *Persistence.*—Do not drop off cleanly.
(7) *Fragrance.*—None.
(8) *Lasting quality.*—On the plant — 3 to 5 days, depending on the weather. As a cut flower — 2 to 4 days.

REPRODUCTIVE ORGANS

A. Stamen, filaments and anthers:
(1) *Arrangement.*—Regularly arranged around styles, shorter than styles.
(2) *Color.*—14C.
B. Pollen: Color: 25B.
C. Styles: Medium length, bunched, generally same length.
D. Stigmas: Color: 154C.
E. Hips:
*Shape.*—Round.
*Size.*—Generally ½ inch diameter.
*Color.*—23B when mature. Seeds do not protrude.

PLANT

A. Form: Upright.
B. Growth: Vigorous.
*Height attained.*—Average of 2 feet.
C. Foliage: Compound normally of 3 to 5 leaflets.
(1) *Size.*—Medium.
(2) *Quantity.*—Abundant.
(3) *Color.*—New foliage: upper side: 143A edged with 61A. under side: 61A. Old foliage: upper side: 137B. under side: 138B.
(4) *Shape.*—Leaflets are teardrop shaped.
(5) *Texture.*—Upper side — Smooth with indented veins. Under side — Raised veins.

(6) *Edge.*—Serrated.
(7) *Serration.*—Uniform indentations.
(8) *Leaf stem.*—Color: Upper side: 137C. Under side: 137D.
(9) *Stipules.*—Short, not bearded.
(10) *Resistance to disease.*—Blackspot — Good. Mildew — Good. Rust — Good.
D. Wood:
(1) *New wood.*—Color — 181A. Bark — Smooth.
(2) *Old wood.*—Color — 139C. Bark — Slightly rough.
E. Thorns (prickles):
(1) *Thorns (prickles).*—Quantity: On main basals/-stalks — few On basal/stalk laterals — usually 1–3 at each internode Form: Flat base, pointed almost straight out from stem. Length: Medium (¼ inch). Color: (when young) 46A. Position: Irregular.
(2) *Prickles.*—On petiole — Generally 2 to 3 On underside of leaflet veins — Few to none These prickles have the same appearance and character but normally are half the overall size of the thorns/prickles on the main and lateral basals/-stalks.
F. Winter hardiness: Protection is needed below 10 degrees Farenheit; mounding canes with soil on leaves should provide the needed protection.

I claim:

1. A new and distinct variety of rose plant of the miniature class, substantially as herein shown and described, characterized particularly by blooms of blended yellow and orange coloration of which varies with light and heat intensity and borne on an upright and vigorous plant with semi-glossy greenlish-purple new foliage and semi-glossy green old foliage, said plant being easy to propagate from cuttings, and said blooms being long-lasting on the plant and as cut flowers.

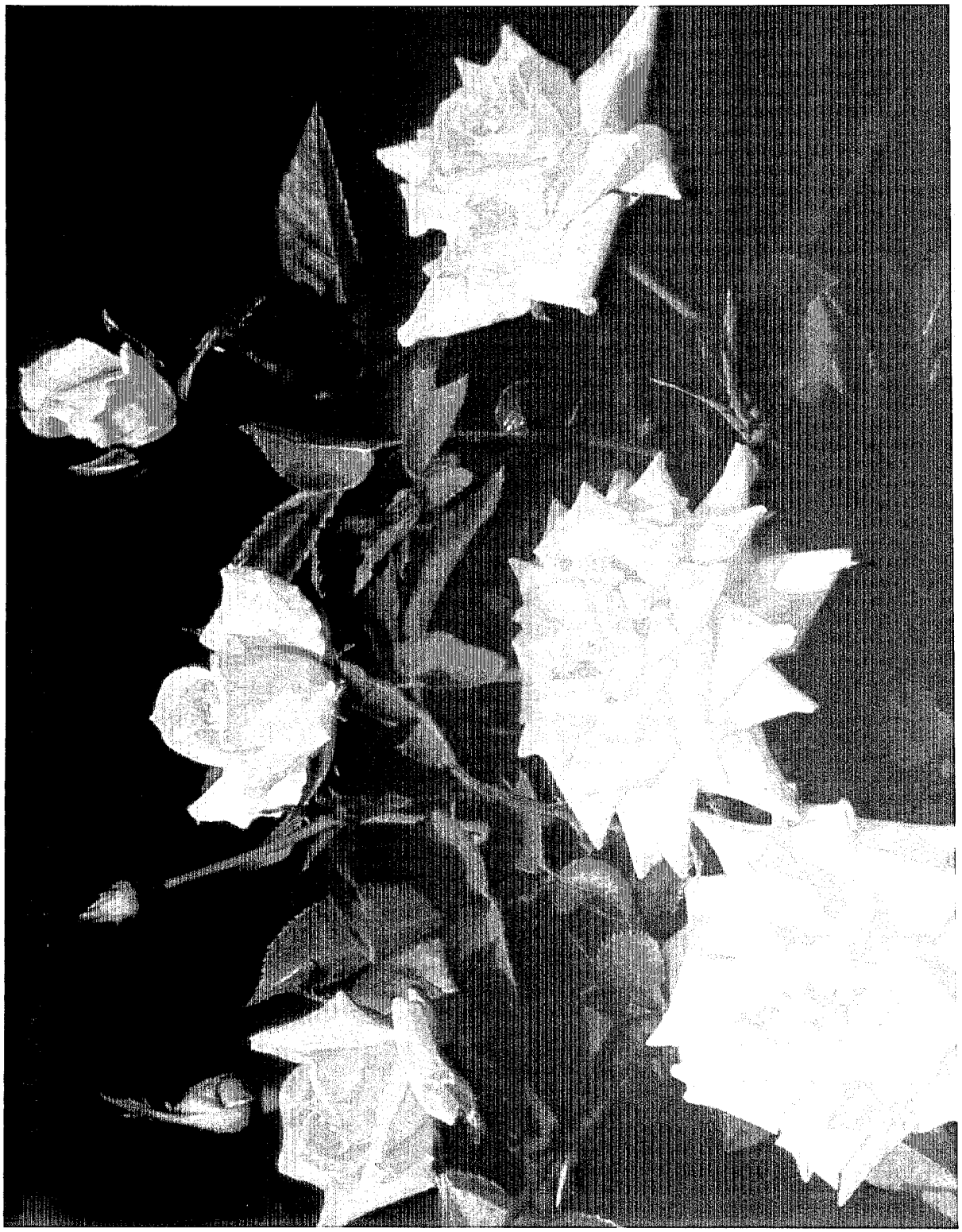

* * * * *